United States Patent [19]

Asnis

[11] Patent Number: 5,059,201
[45] Date of Patent: Oct. 22, 1991

[54] SUTURE THREADING, STITCHING AND WRAPPING DEVICE FOR USE IN OPEN AND CLOSED SURGICAL PROCEDURES

[76] Inventor: Stanley E. Asnis, 38 Cornwall La., Port Washington, N.Y. 11050

[21] Appl. No.: 644,677

[22] Filed: Jan. 22, 1991

Related U.S. Application Data

[63] Continuation of Ser. No. 544,042, Jun. 26, 1990, abandoned, which is a continuation of Ser. No. 432,138, Nov. 3, 1989, abandoned.

[51] Int. Cl.⁵ ............................................. A61B 17/00
[52] U.S. Cl. ................................... 606/144; 606/139; 606/146; 606/148
[58] Field of Search ............................. 606/138–140, 606/144, 146, 148

[56] References Cited

U.S. PATENT DOCUMENTS

| | | | |
|---|---|---|---|
| 1,037,864 | 9/1912 | Carlson . | |
| 1,449,087 | 3/1923 | Bugbee . | |
| 1,635,066 | 7/1927 | Wells . | |
| 1,815,725 | 7/1931 | Pilling . | |
| 1,822,330 | 9/1931 | Ainslie . | |
| 1,856,721 | 5/1932 | Nagelmann . | |
| 2,457,379 | 12/1948 | Kallenbach | 606/146 |
| 2,579,192 | 12/1951 | Kohl | 606/144 |
| 2,813,736 | 11/1957 | Archer et al. | 606/144 |
| 2,959,172 | 11/1960 | Held . | |
| 3,470,875 | 10/1969 | Johnson . | |
| 3,842,840 | 10/1974 | Schweizer . | |
| 3,901,244 | 8/1975 | Schweizer . | |
| 3,946,740 | 3/1976 | Bassett . | |
| 4,164,225 | 8/1979 | Johnson . | |
| 4,224,947 | 9/1980 | Fukuda . | |
| 4,312,337 | 1/1982 | Donohue . | |
| 4,596,249 | 6/1986 | Freda . | |
| 4,602,635 | 7/1986 | Mulhollan et al. | 606/144 |
| 4,712,545 | 12/1987 | Honkanen | 606/208 |
| 4,836,205 | 6/1989 | Barrett | 606/144 |
| 4,890,615 | 1/1990 | Caspari et al. | 606/146 |

FOREIGN PATENT DOCUMENTS 549146 12/1973 U.S.S.R. .............................. 606/139

*Primary Examiner*—Stephen C. Pellegrino
*Assistant Examiner*—Gary Jackson
*Attorney, Agent, or Firm*—Pandiscio & Pandiscio

[57] ABSTRACT

A surgical instrument for threading a loop of suture material through a piece of tissue to be stitched or removed as part of a surgical procedure and for wrapping a loop of suture around a piece of tissue. The instrument includes an extractor shaft assembly which is slidably disposed inside an inner tube. The latter is slidably disposed inside an outer tube. The extractor assembly has a pointed front end and a hook directly behind the front end. A tissue clamping bracket is secured to the front end of the outer tube, both of which are sized to fit inside a conventional cannula of the sort used in closed surgeries. The outer tube is secured to a handle assembly which includes a movable member for causing the inner tube to reciprocate inside the outer tube so as to coact with the clamping bracket to clamp a piece of tissue therein. By proper manipulation of the extractor assembly, a suture segment which is secured to the front of the clamping bracket can be captured and pulled through or over a piece of tissue clamped in the bracket and formed into a slip knot stitch which can be closed about the tissue piece.

20 Claims, 6 Drawing Sheets

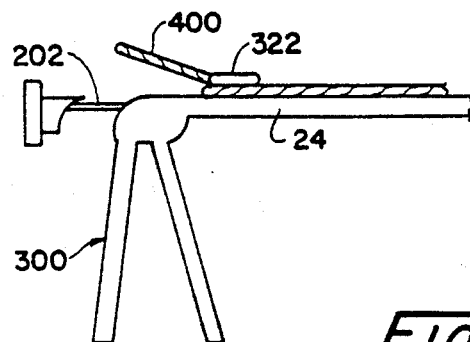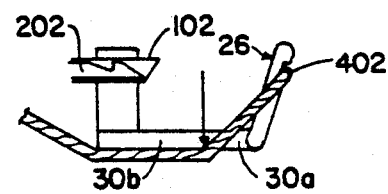
Fig. 10
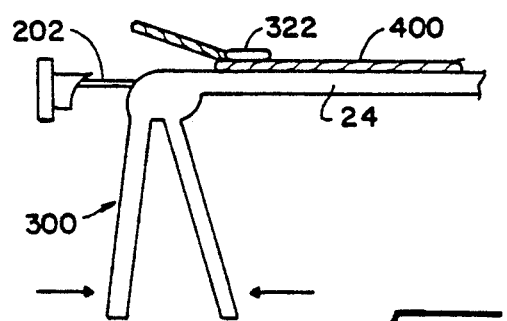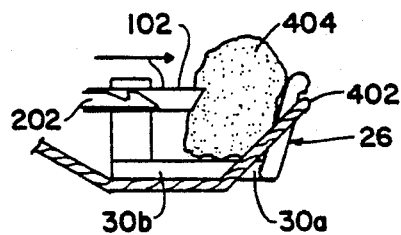
Fig. 11
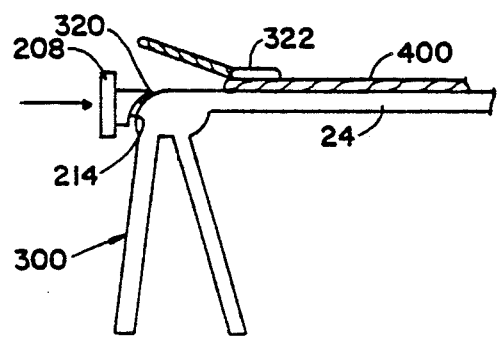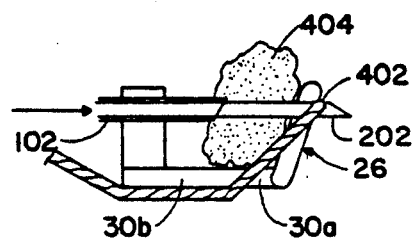
Fig. 12

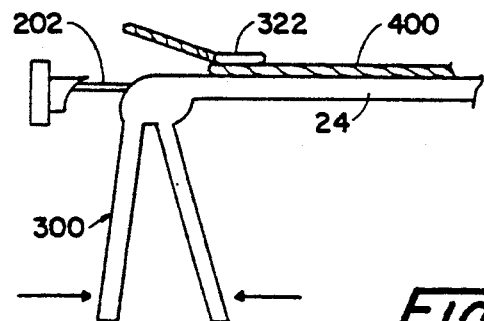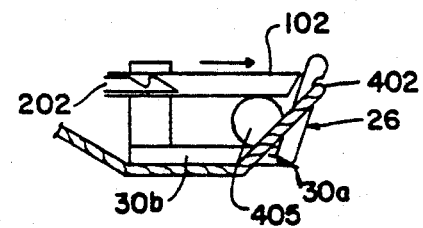
Fig. 16
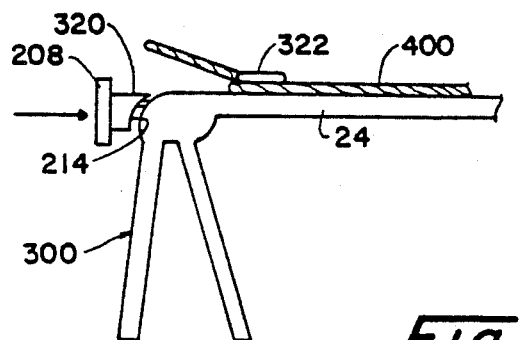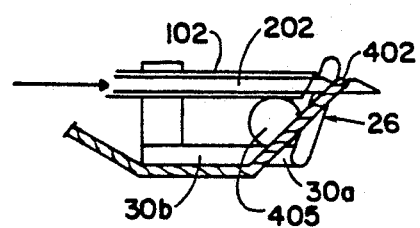
Fig. 17
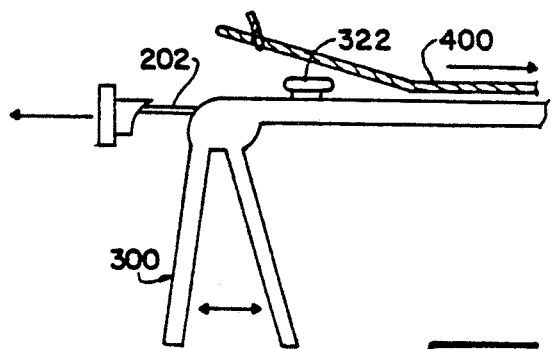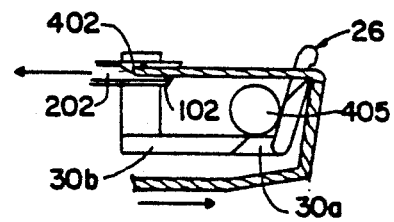
Fig. 18

SUTURE THREADING, STITCHING AND WRAPPING DEVICE FOR USE IN OPEN AND CLOSED SURGICAL PROCEDURES

This is a continuation of U.S. patent application Ser. No. 07/544,042, filed Jun. 26, 1990 by Stanley E. Asnis for Suture Threading, Stitching and Wrapping Device For Use In Open and Closed Surgical Procedures, which is itself a continuation of U.S. patent application Ser. No. 07/432,138, filed Nov. 3, 1989 by Stanley E. Asnis for Suture Threading, Stitching and Wrapping Device For Use In Open and Closed Surgical Procedures both now abandoned.

FIELD OF THE INVENTION

This invention relates generally to surgical instruments, and more particularly to surgical punches, forceps, and suture threading, stitching and wrapping instruments.

BACKGROUND OF THE INVENTION

Surgical punches and forceps are well known in the art, as illustrated by the surgical punch and surgical forceps disclosed in U.S. Pat. No. 4,712,545 issued to G. Honkanen. Such instruments are frequently used in arthroscopic and other surgeries to cut and clamp, respectively, body tissue.

In typical arthroscopic, laparascopic and other surgical procedures, cartilage or other tissue is clamped, cut, shaved or otherwise formed using special surgical tools which are sized so as to allow the tools to extend into an interior surgical site (i.e., the interior of a joint) from a point outside the body through an opening-lining tube or cannula. Often, a saline wash is pumped into the surgical site through an inlet cannula and out of the surgical site through an outlet cannula.

As part of both open and closed surgical procedures, it is often necessary to remove severed cartilage or other tissue material from the surgical site. Absent such removal, the severed pieces of tissue can lodge in the joint being operated on and cause irritation, degeneration and pain.

In the past, in closed surgeries (e.g. arthroscopy), it has frequently been difficult to sever and then extract a piece of cartilage or tissue through one of the cannulae used in the closed-surgery procedure. In a typical procedure, the piece of tissue which is to be removed is first clamped, e.g. with forceps, to prevent the latter from escaping once cutting is effected, and then a punching or other severing device is used to detach the selected piece of tissue from the remaining tissue. Unfortunately, because the forceps or other clamping device often surrounds some or all of the piece of tissue which is to be removed, it is often difficult, if not impossible, to bring the punching or severing device into the desired contact with the tissue. On the other hand, if the piece of tissue is not clamped prior to removal, the tissue may escape once it is cut free, to thereafter lodge in some undesirable location. Thus, known surgical punches and forceps are typically not well adapted for cutting and removing a selected piece of body tissue from a closed surgical site.

In both open and closed surgical procedures, it is also frequently necessary to place a suture stitch in a piece of tissue, or to stitch together pieces of tissue with suture material. In closed surgeries, such as arthroscopy, it is difficult using conventional straight or curved suture needles to stitch suture material through a piece of tissue. In open surgeries, it is frequently difficult using a conventional straight or curved suture needle to stitch a piece of tissue where there is insufficient room behind the tissue to pass the suture needle. Furthermore, in both open and closed surgeries, it is often difficult to wrap a piece of tissue, such as a ligament, located in a relatively inaccessible region of the surgical site, with a piece of suture material using conventional surgical instruments.

OBJECTS OF THE INVENTION

Accordingly, one of the objects of the present invention is to provide a surgical suture threading, stitching and wrapping device for use in open and closed surgeries for (1) threading a loop of suture material through a piece of tissue which is to be removed during a subsequent severing operation, or (2) placing a suture stitch in a piece of material or stitching together several pieces of tissue, or (3) wrapping a piece of suture material around a soft tissue structure such as ligaments, tubes or ducts.

Another object of the invention is to provide a surgical suture threading, stitching and wrapping device which is sized so as to be able to extend through a conventional cannula used in closed surgeries (e.g. arthroscopy) and which is operable from a location adjacent the outside opening of the cannula or soft tissue portal.

Yet another object of the present invention is to provide a surgical suture threading, stitching and wrapping device having a novel clamp assembly for clamping a piece of tissue while suture material is simultaneously being threaded through the piece of tissue.

Still another object of the present invention is to provide a surgical suture threading, stitching and wrapping device having a novel threading assembly for threading a loop of suture material through a piece of tissue and forming a slip knot stitch which can be closed about the tissue piece.

SUMMARY OF THE INVENTION

These and other objects are achieved by a novel tool having a clamping assembly for clamping a piece of tissue and a threading assembly for threading a loop of suture material through or around the clamped piece of tissue.

The clamping assembly comprises an outer tube, an inner tube disposed for slidable movement inside the outer tube, a U-shaped bracket attached to the outer tube at one end thereof, and an actuating assembly for moving the inner tube toward and away from the U-shaped bracket. The U-shaped bracket is constructed so that a piece of tissue to be threaded, stitched or wrapped can be received between the legs of the bracket. By proper manipulation of the actuating assembly, the inner tube is driven forward so as to clamp the piece of tissue between the inner tube and one leg of the U-shaped bracket.

The threading assembly comprises a pointed shaft slidably disposed in the inner tube. The pointed shaft has a hook at its pointed end for engaging a length of suture. An aperture is provided in the leg of the U-shaped bracket against which the piece of tissue is clamped for receiving the pointed shaft, and a groove is provided in the outer surface of this bracket leg for receiving a segment of a loop of suture.

When it is desired to thread or stitch a piece of tissue, a loop of suture is secured in the groove in the front leg or front wall of the U-shaped bracket so as to extend rearward from the groove. Then the tool is inserted through the cannula to the surgical site, and the tool is positioned so that the target tissue is inserted in the U-shaped bracket. Then the inner tube is driven forward so as to clamp the piece of tissue between the front end of the inner tube and the front leg of the U-shaped bracket. Then a loop of suture is threaded through the clamped piece of tissue by (1) forcing the pointed shaft through the clamped tissue material and through the aperture in the bracket leg, whereby the shaft's hook may engage the suture, and (2) then pulling the engaged suture through the aperture and the hole in the tissue formed by the shaft.

When it is desired to wrap a piece of suture around a piece of tissue such as a ligament, tube or duct, a loop of suture is secured in the groove in the bracket so as to extend rearward from the groove. The tool is inserted through the cannula to the surgical site, and the tool is positioned so that the target tissue is positioned on the base or bottom wall of the U-shaped bracket. Then the inner tube is driven forward toward the front leg of the U-shaped bracket so as to clamp the piece of tissue between the base of the U-shaped bracket and the bottom side of the front end of the inner tube. Then the pointed shaft is (1) moved forward inside the inner tube so as to pass over the clamped tissue piece and through the aperture in the bracket, whereby the shaft's hook engages the suture, and (2) the engaged suture is pulled back over the tissue piece with the result that the loop of suture is wrapped around the tissue piece.

BRIEF DESCRIPTION OF THE DRAWINGS

Still other objects and features of the present invention will be more fully discussed or rendered obvious in the following detailed description of the invention which is to be considered together with the accompanying drawings wherein like numbers refer to like parts and further wherein:

FIG. 10 is a schematic side elevation of the present invention, with a loop of suture material secured around the bracket;

FIG. 11 is similar to FIG. 10, except that a piece of tissue is disposed in the clamping bracket and the inner tube has been moved forward so as to clamp the tissue in the bracket;

FIG. 12 is similar to FIG. 11, except that the hook end of the extractor has been urged through the clamped tissue;

FIG. 16 is similar to FIG. 11, except that an elongate tissue piece having a circular cross section is clamped between the bottom of the bracket and the bottom of the inner tube;

FIG. 17 is similar to FIG. 16, except that the extractor has been urged over the clamped piece of tissue; and FIG. 18 is similar to FIG. 17, except that the hook end of the extractor of suture has been pulled over the piece of tissue and into the inner tube bringing with it the loop of suture material secured around the bracket.

DETAILED DESCRIPTION OF THE INVENTION

Figure 1:
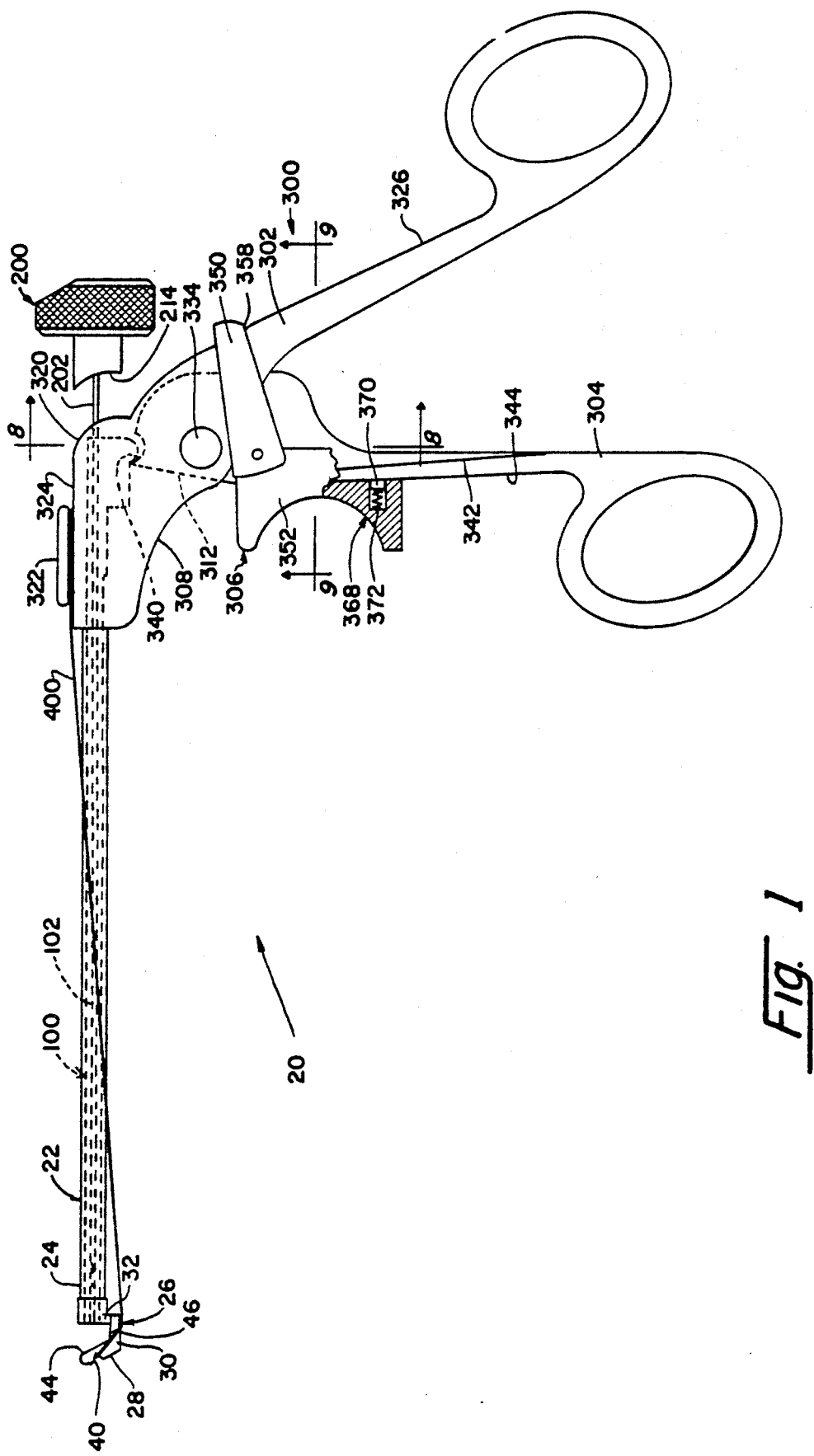
FIG. 1 is a side elevation view of the suture stitching, threading and wrapping device of the present invention, partially in cross section, with portions of the device being shown in phantom.

Referring to FIG. 1, the suture threading, stitching and wrapping device 20 of the present invention comprises an outer tube assembly 22, an inner tube assembly 100, an extractor assembly 200, and a housing and inner tube actuation assembly 300. The various elements of device 20 are preferably made from a corrosion-resistant material, such as stainless steel.

Outer tube assembly 22 comprises a hollow tube 24 and a clamping bracket 26 secured to the distal end of the tube. The diameter of tube 24 and the cross-sectional dimensions of bracket 26 are selected so that the elements may be readily inserted into a conventional cannula of the type used in arthroscopy or other closed surgeries. The length of tube 24 is selected so that the latter may extend from a position inside the joint being operated on to a position outside the opening of the cannula in which the device 20 is inserted. This length of tube 24 is also advantageous in open surgeries when the tissue piece to be threaded, stitched or wrapped is deeply recessed.

Figure 2:
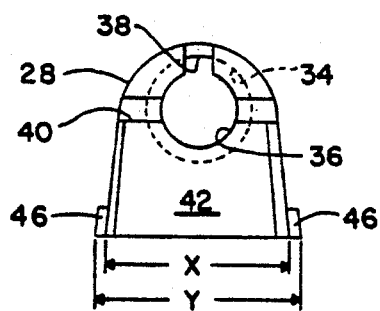
FIG. 2 is a front elevation view of the tissue-clamping bracket.
Figure 3:
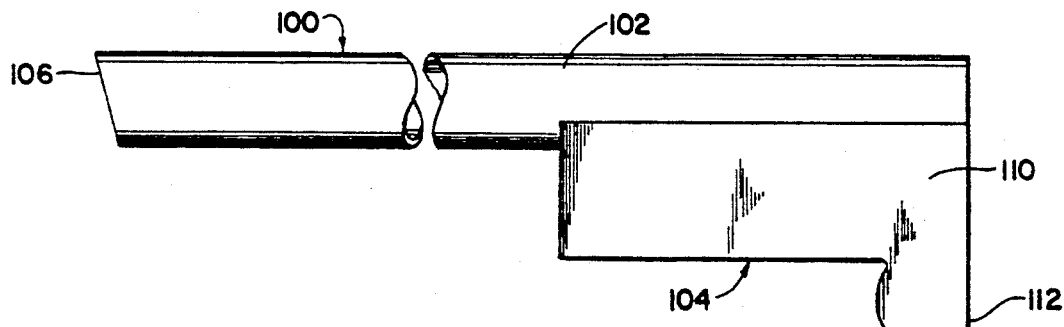
FIG. 3 is a side elevation view of the inner tube.
Figure 4:
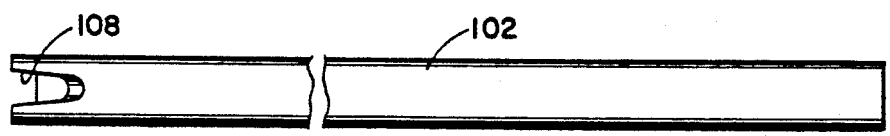
FIG. 4 is a plan view of the inner tube illustrated in FIG. 3.

Referring next to FIGS. 1 and 2, clamping bracket 26, when viewed in side elevation as in FIG. 1, has a substantially U-shaped configuration. Bracket 26 has a front leg or wall 28, a bottom wall or base 30 and a rear leg or wall 32. Clamping bracket 26 is attached to the distal end of outer tube 24 via its rear wall 32. The latter includes a bore 34 (FIG. 2) extending therethrough. Bore 34 is sized to receive inner tube 102 with a sliding fit, as described hereinafter.

Front wall 28 is preferably inclined forwardly slightly relative to rear wall 32, i.e., away from actuation assembly 300, and is substantially coaxially aligned with tube 24. A circular hole 36 (FIG. 2) is provided in front wall 28 extending entirely therethrough. Hole 36 is coaxially aligned with bore 34 in rear wall 32 and is sized to receive extractor shaft 202 with a sliding fit, as described hereinafter. A vertically-extending slot 38 is provided in front wall 28 intersecting hole 36. A horizontally-extending groove 40 is provided in front surface 42 of front wall 28. Grove 40 extends across the center of hole 36 and is sized to receive a length of suture of the type used in surgery. Front wall 28 has an inside surface 44 (FIG. 1) opposite front surface 42.

Figure 13:
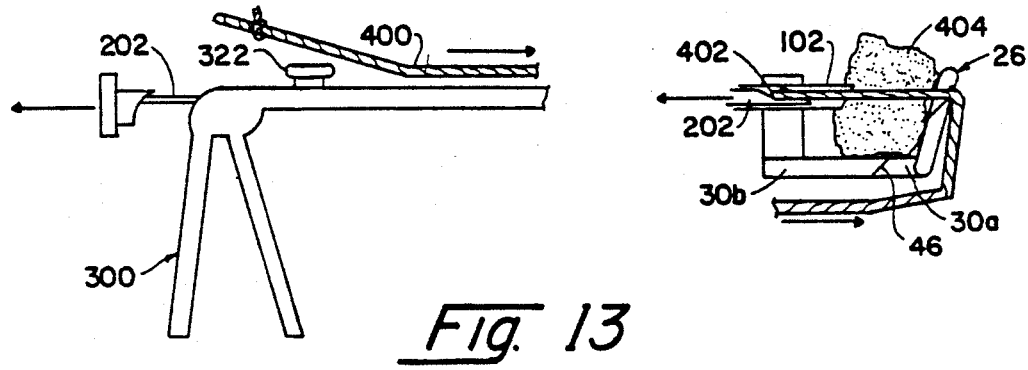
FIG. 13 is similar to FIG. 12, except that the hook end of the extractor has been pulled through the tissue and into the inner tube bringing with it the loop of suture material secured around the bracket.

The width X (see FIG. 2) of front wall 28 and the front portion 30a (see FIG. 13) of bottom wall 30 is less than the width Y (see FIG. 2) of the rear portion 30b (see FIG. 13) of bottom wall 30. As a result of this configuration, a shoulder 46 (see FIGS. 1, 2 and 13) is formed at the junction of the front and rear portions of bottom wall 30. Preferably, this shoulder in inclined forwardly toward front wall 28 so as to subtend an angle ranging from 45° to 70° with respect to the bottom surface of bottom wall 30.

Referring next to FIGS. 1 and 3-5, inner tube assembly 100 comprises tube 102 and pivot assembly 104. Tube 102 is sized to slide freely inside outer tube 24. The length of tube 102 is selected so that when the latter is received in outer tube 24, the front end 106 of tube 102 will project forwardly of rear wall 32 of bracket 26 a selected distance when the actuating assembly 300 is properly manipulated, as described hereinafter. When tube 102 is in this forwardly projecting position, bottom wall 30 of bracket 26 is spaced somewhat from the bottom of tube 102. Front end 106 is preferably inclined forwardly slightly an amount corresponding to the inclination of front wall 28. This inclination is selected so that bracket inside surface 44 and tube front end 106 extend substantially in parallel with one another when inner tube assembly 100 is pivotally mounted to actuating assembly 300, as described hereinafter. A V-shaped notch 108 (FIG. 4) is provided in the top surface of tube 102 intersecting front end 106.

Figure 5:
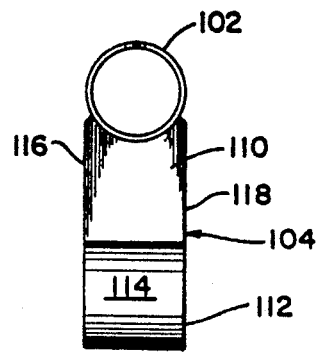
FIG. 5 is a front elevation view of the tube illustrated in FIGS. 3 and 4.

Pivot assembly 104 comprises a rectangular block 110 secured to the bottom surface of tube 102 at the back end thereof. As best seen in FIG. 5, the thickness of block 110 is about equal to the outside diameter of tube 102. Pivot assembly 104 includes a bottom projection 112 having a circularly curved outer pivot surface 114 of selected radius of curvature. The thickness of projection 112 is substantially identical to the thickness of block 110. As such, the side surfaces of block 110 and projection 112 are coextensive, which side surfaces are identified at 116 and 118 in FIG. 5. The side surfaces 116 and 118 of block 110 and projection 112 are substantially planar and extend in parallel with one another.

Figure 6:
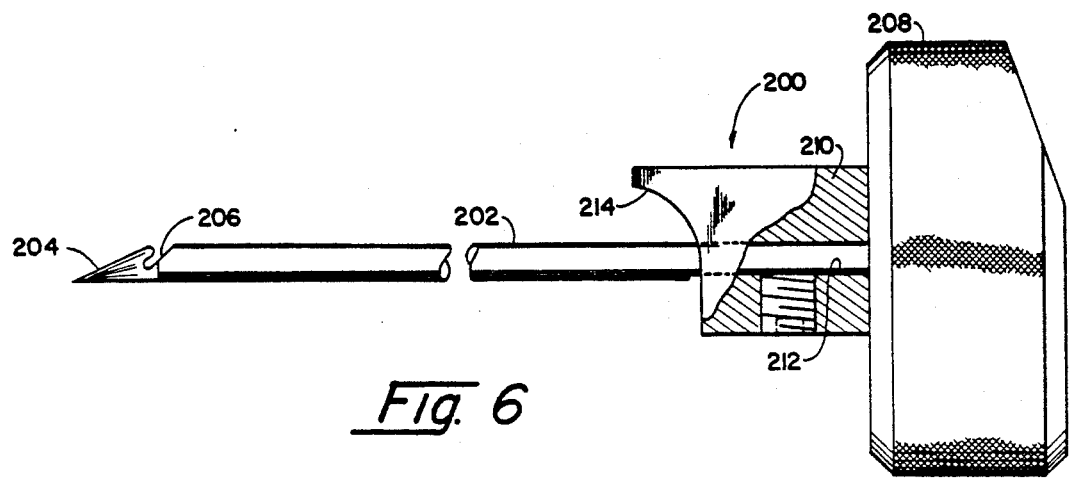
FIG. 6 is a side elevation of the suture extractor.
Figure 7:
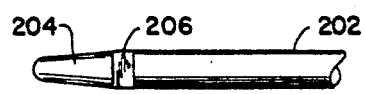
FIG. 7 is a plan view of the front portion of the extractor illustrated in FIG. 6.

Referring next to FIGS. 6 and 7, extractor assembly 200 comprises a shaft 202 that is sized to slide freely inside inner tube 102. Shaft 202 has a pointed front end 204. A slot 206 is provided in the top surface of shaft 202 directly behind front end 204. Slot 206 extends transversely to the longitudinal axis of the shaft and is angled forwardly toward the front of shaft 202. Slot 206 is sized to accept a length of conventional suture of the type used in surgery.

Extractor assembly 200 includes a knurled knob 208 for facilitating manipulation of shaft 202. Knob 208 is attached to projection 210, and the latter has a bore 212 in which the back end of shaft 202 is releasably secured by suitable means, e.g. a set screw. Projection 210 includes a curved contact surface 214 for engaging actuating assembly 300 so as to limit the travel of shaft 202 and maintain the rotational orientation of shaft 202, as described hereinafter. The length of shaft 202 is selected and projection 210 is provided so that only a selected length of shaft 202, typically front end 204, will extend through and past the front surface of bracket front wall 28. Preferably, this selected distance ranges from about 0.125 to 0.375 inches.

Figure 8:
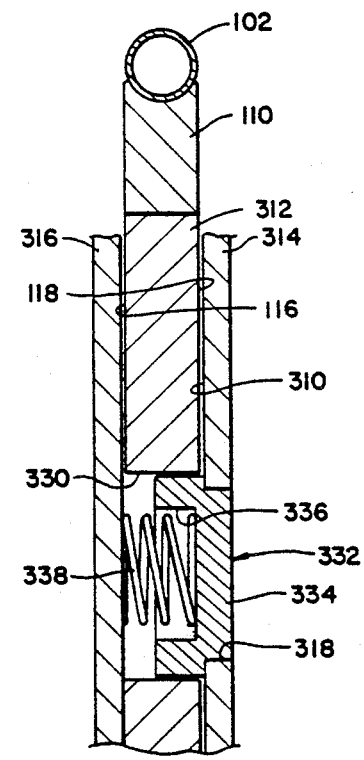
FIG. 8 is a cross-sectional view of the actuating assembly taken along line 8—8 in FIG. 1.

Referring next to FIGS. 1 and 8, actuating assembly 300 comprises a fixed scissors-type handle 302, a movable scissors-type handle 304 pivotally mounted to the fixed handle, and a locking member 306 for locking the movable handle in a selected position relative to the fixed handle. Handles 302 and 304 are constructed to extend away from one another in V-shaped configuration when fully open, and to extend substantially in parallel with one another when fully closed.

Fixed handle 302 includes an upper portion 308 to which the back end of outer tube 102 is attached. A cavity 310 (FIG. 8) is provided in upper portion 308. Upper portion 308 comprises a first opening (not shown) through which inner tube assembly 100 can be inserted into cavity 310 and a second opening 311 (FIG. 9) through which top end 312 of movable handle 304 can be inserted into cavity 310. Upper portion 308 also includes parallel sidewalls 314 and 31 (FIG. 8) which enclose cavity 310. Sidewalls 314 and 316 are spaced apart a distance sufficient to accommodate inner tube pivot portion 104 therebetween with a close sliding fit. A pivot bore 318 (FIG. 8) is provided in sidewall 314. Upper portion 308 includes a curved contact surface 320 (FIG. 1) having a curvature that corresponds to the curvature of curved surface 214 of projection 210.

Upper portion 308 includes a clamp 322 (FIG. 1). The latter is attached via a center stud (not shown) to the top surface 324 of upper portion 308 so that a small space is provided between the top surface and the bottom of the clamp. This space is of sufficient dimension to permit a conventional suture to be wrapped around the clamp stud and to be secured to clamp 322 by friction engagement between the bottom of the clamp and the top surface 324 of upper portion 308. A serrated surface 326 (FIG. 1) is provided on the rear surface of fixed handle 302.

Top end 312 of movable handle 304 comprises a pivot bore 330 (FIG. 8) having a diameter that is somewhat greater than the diameter of pivot bore 318 in sidewall 314 of upper portion 308. As illustrated in FIGS. 1 and 8, the top end 312 of fixed handle 304 is disposed in cavity 310 so that bore 330 is coaxially aligned with bore 318.

Actuating assembly 300 includes a cylindrical pivot stud 332 for pivotally mounting fixed handle 302 to movable handle 304. Stud 332 is mounted in bore 330. The diameter of stud 332 is selected so that the latter makes a close sliding fit in bore 330. Stud 332 includes a reduced diameter circular portion 334 that is sized to make a close sliding fit in bore 318. Stud 332 includes a cavity 336 in which one end of coil spring 338 is disposed. The opposite end of spring 338 contacts the inner surface of sidewall 316 of upper portion 308. Spring 338 forces stud 332 into contact with sidewall 314 and stud portion 334 into bore 318.

Top end 312 of movable handle 304 includes a curved pocket 340 (FIG. 1) sized for receiving curved projection 112 (FIG. 3) of inner tube assembly 100. The configuration of pocket 340 is selected to permit projection 112 to pivot freely therein, as described hereinafter, about an axis extending substantially normal to sidewalls 314 and 316 of upper portion 308.

Movable handle 304 includes an upstanding ridge 342 (FIG. 1) which extends along the length of the handle. Movable handle 304 also includes a front surface 344 (FIG. 1) that extends along the length thereof.

Figure 9:
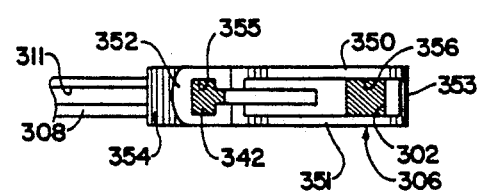
FIG. 9 is cross-sectional view of the actuating assembly taken along line 9—9 in FIG. 1.

Referring now to FIGS. 1 and 9, locking member 306 surrounds and is disposed for slidable movement along handles 302 and 304. Member 306 is of hollow construction and includes a pair of identical sidewalls 350 and 351 (FIG. 9), a front section 352, and a rear wall 353 (FIG. 9). Front section 352 includes a C-shaped fingergrip depression 354 sized to accept a finger of the user of the present tool. Front section 352 also has an interior opening 355 that accommodates ridge 342 of fixed handle 304 and an interior slot 356 that accommodates movable handle 302. Front section 352 further includes one or more biasing assemblies 368 (FIG. 1) for preventing the front section from binding as it slides along movable handle 304. The assembly 368 preferably comprises an anti-friction pad 370 and a compression spring 372, both of which are disposed in a bore provided in the front section 352. The compression spring 372 forces the anti-friction pad 370 into engagement with the front surface 344 of movable handle 304.

Rear wall 353 is formed with a right angle corner edge 358 (FIG. 1) for engaging the serrations 326 on fixed handle 302.

In the following description of the operation of the instrument of the present invention, reference should be made to FIGS. 1–18. For the purpose of this description, it is assumed device 20 is in the fully-assembled state illustrated in FIG. 1. In this state, movable handle 304 is pivotally mounted to fixed handle 302 via stud 332. Curved projection 112 of inner tube assembly 100 is positioned in pocket 340 of top end 312 of movable handle 304. Extractor shaft 202 is disposed inside inner tube 102 and is positioned so that its curved contact surface 214 is spaced a selected distance from the curved contact surface 320 of fixed handle 302. The length of shaft 202 is selected so that when the latter is in this position, its pointed front end 204 does not project forwardly of rear wall 32 of bracket 26. Lock member 306 surrounds handles 302 and 304 and is positioned near the upper ends of the handles adjacent pivot stud 332. The handles 302 and 304 are spaced apart from one another as far as locking member 306 will permit, i.e., they are in the "unclamped" position. The length of inner tube 102, the configuration of top end 312 of movable handle 304, and the placement of pocket 340 in top end 312 are selected so that when the handles 302 and 304 are in the unclamped positioned, front end 106 of inner tube 102 does not project forwardly of rear wall 32 of bracket 26.

Initially, use of the instrument of the present invention to thread or stitch a piece of tissue will be described. In connection with this description, reference should be made to FIGS. 10–15. Thereafter, the manner in which the instrument is used to wrap a suture around an elongate piece of tissue such as a ligament will be described. In connection with this description, reference should be made to FIGS. 16–18.

To use the instrument of the present invention to thread or stitch a piece of suture in a piece of tissue, a loop of suture 400, the free ends of which are knotted together, is secured to the instrument by positioning a mid-length segment 402 of the loop in groove 40 in the front wall 28 of bracket 26. The loop 400 is then tensioned and the loop is secured to clamp 322, so as to maintain tension on the loop, by forcing the loop between the bottom of the clamp and top surface 324 of upper portion 308. Preferably, the loop 400 is wrapped around the clamp 322 several times so as to increase the length of suture clamped thereto, which in turn ensures the loop will remain securely attached to the clamp.

Additional tension is then applied to loop 400 by moving the portion of the loop immediately rearward of the mid-length section 402 of the loop so that it engages (1) shoulder 46 and (2) the outermost edges of the bottom surface of the rear portion 30b of bottom wall 30, as illustrated in FIG. 10. In addition to increasing the tension on loop 400, by positioning the front portion of the loop so that it engages shoulder 46, the loop is supported below the interior U-shaped surface of clamping bracket 26. By supporting the loop 400 in this manner, a piece of tissue can be easily inserted into the bracket and moved into contact with the top surface of bottom wall 30 without interfering with the loop. If the loop 400 is not moved to pass around shoulder 46, then insertion of tissue into bracket 26 also involves manipulating the bracket relative to the tissue so as to cause the latter to force the front portion of loop 400 downwardly toward the top surface of bottom wall 30.

Next, for closed surgery (e.g. arthroscopy), the outer tube assembly 22, with the inner tube 102 and extractor shaft 202 disposed therein, is inserted into a skin portal or a cannula (not shown) extending into the closed surgical site. Using known closed surgery surgical viewing systems, typically fiber optic systems, the user of the instrument manipulates the latter so as to position a piece of tissue 404 (e.g. a piece of meniscal tissue) which is to be threaded or stitched between walls 28 and 32 of bracket 26 and in contact with bottom wall 30 of bracket 26, as illustrated in FIG. 11. For open surgery, the device is inserted into the surgical site and is manipulated, typically based on direct observation, until the piece of tissue 404 is received between walls 28 and 32 of bracket 26 and is in contact with bottom wall 30 of bracket 26, as illustrated in FIG. 11. When tissue piece 404 is positioned in this manner, loop of suture 400 extends rearwardly from groove 40 beneath tissue piece 404.

As the next step, movable handle 304 is squeezed toward fixed handle 302 causing the former to pivot about stud 332. This pivotal motion drives pocket 340 of top end 312 forward toward bracket 26. As pocket 340 moves forward, it carries projection 112 disposed therein forward. During this forward movement of projection 112, the latter pivots inside pocket 340, about an axis that extends normal to sidewalls 314 and 316, with the curved surface 114 of projection 112 sliding along the curved surface of pocket 340. In the event inner tube 102 begins to rotate about its longitudinal axis during the forward or rearward movement of projection 112, sidewalls 314 and 316 of upper portion 304 will slidingly engage side surfaces 118 and 116, respectively, of top end 312 of movable handle 304 and thereby prevent rotation of tube 102. Consequently, front end 106 of inner tube 102 always extends approximately in parallel with inside surface 44 of leg 28 of bracket 26.

As noted above, projection 112 is attached via block 110 to inner tube 102. As such, when movable handle 304 is squeezed toward fixed handle 302, driving projection 112 forward, inner tube 102 is driven forward. The length of inner tube 102 is selected so that when handle 304 is moved a selected distance toward handle 302, which distance will vary with the thickness of tissue piece 404, front end 106 of inner tube 102 is driven against tissue piece 404. In turn, tissue piece 404 is forced against inside surface 44 of bracket leg 28 so as to clamp the tissue piece between bracket front wall 28 and tube 102. This clamping action is illustrated in FIG. 11.

Thereafter, locking member 306 is slid down handles 302 and 304 until the latter are wedged within the locking member. As noted above, handles 302 and 304 extend away from one another in V-shaped configuration when fully open and extend substantially in parallel to one another when fully closed. As such, the handles provide a V-shaped wedge which the locking member frictionally engages when moved into frictional contact with the handles. The position where this contact occurs will, of course, vary with the thickness of the tissue piece 404 clamped in bracket 26. Serrated surface 326 is provided on movable handle 302 for ensuring locking member 306 remains frictionally engaged with the handles 302 and 304. Right angle corner 358 on locking member 306 is received between serrations on serrated surface 326 when the locking member frictionally engages handles 302 and 304, whereby a positive engagement is achieved between the locking member 306 and the fixed handle 304. After locking member 306 has been moved into frictional engagement with handles 302 and 304, the latter can be released and tissue piece 404 will remain clamped within bracket 26.

Then, extractor assembly 200 is urged forward within inner tube 102 toward the clamped tissue piece 404 until curved contact surface 214 of extractor assembly 200 engages curved contact surface 320 of upper portion 308. Typically, this forward movement is achieved by pressing forward on extractor knob 208. As extractor assembly 200 is pressed forward, its pointed end 204 will pass through bore 34 in bracket rear wall 32, through tissue piece 404 and through bore 36 in bracket front wall 28, as illustrated in FIG. 12. As noted above, the length of extractor shaft 202 is selected and projection 210 is provided so that only a front portion of the latter, measuring about 0.125 to 0.375 inch in length, extends beyond front surface 42 of bracket front wall 28. Curved contact surface 214 of extractor assembly 200 and curved contact surface 320 of upper portion 308 are configured to ensure that extractor assembly 200 assumes a predetermined rotational alignment when surface 214 engages surface 320. When so rotationally aligned, slot 206 of shaft 202 is on top of the shaft.

Next, the suture loop is unclamped from clamp 322 and is preferably held under tension by the user of the instrument to ensure segment 402 of the suture loop remains disposed within groove 40. Extractor assembly 200 is then caused to move rearwardly in the inner tube 102 by pulling rearwardly on extractor knob 208. As extractor shaft 202 is moved rearwardly, slot 206 in shaft 202 passes beneath suture segment 402 and the latter either drops into slot 206 or is caught and forced into slot 206. Thus, pointed end 204 and slot 206 together comprise a hook or barb for capturing suture segment 402. In some cases, suture segment 402 may be captured in slot 206 when shaft 202 first pierces through tissue piece 404. As extractor assembly 200 is pulled rearwardly, its pointed end 204 passes back through tissue piece 404 and into inner tube 102. Because suture segment 402 is captured in slot 206, as extractor shaft 202 is moved rearwardly, segment 402 is drawn through the tissue piece 404 and into inner tube 102. During this rearward movement of the extractor assembly 200, the user of the present instrument will pay out the suture loop 400 to permit the latter to be drawn into inner tube 102.

Figure 14:
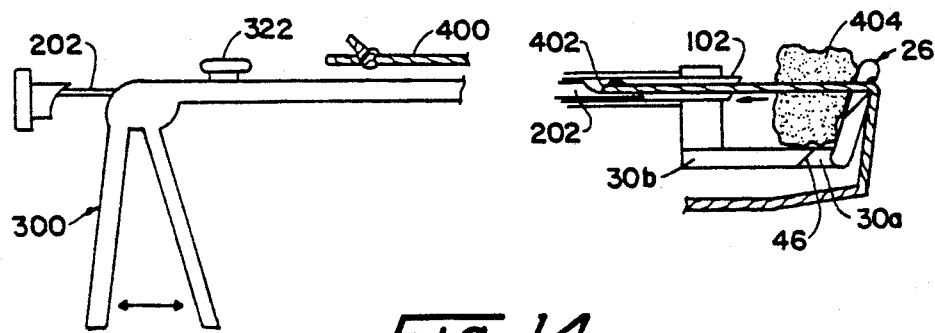
FIG. 14 is similar to FIG. 13, except that the outer clamping member has been moved rearward so that it does not engage the tissue.
Figure 15:
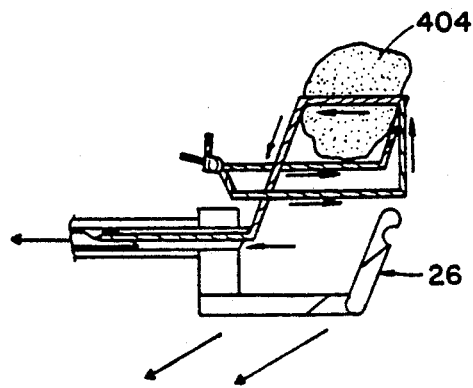
FIG. 15 is similar to FIG. 14, except that the tissue-clamping bracket has been disengaged from the tissue.

After extractor assembly 202 has been moved rearwardly into outer tube 102 a distance such that its pointed end 204 is positioned rearwardly of the inner surface of rear wall 32, locking member 306 is moved back up handles 302 and 304 toward pivot stud portion 332, and the handles are moved apart from one another. As handle 304 is moved away from handle 302, pocket 340 is moved rearwardly. This rearward movement, in turn, causes inner tube 102 to move rearwardly out of clamping engagement with tissue piece 404, as illustrated in FIG. 14. Clamping bracket 26 is then manipulated to disengage tissue portion 404 therefrom. The present instrument 20 is then extracted from the cannula, when used in closed surgeries, or from the surgical site in open surgeries, in which it was positioned during the above-described procedure.

As instrument 20 is extracted from the surgical site, captured loop segment 402 is pulled away from tissue piece 404 thereby causing suture 400 to be drawn further through the tissue piece. At this juncture, the portion of suture 400 being drawn through the tissue may be passed through the loop of suture formed at the knotted end of suture 400 so as to form a slip knot stitch. A point is reached during the extraction of instrument 20 where the slip knot stitch will be drawn closed around tissue piece 404.

Upon completion of the foregoing procedure, the extractor assembly 202 is urged forward so that slot 206 projects out of the front end of outer tube 102. Midlength section 402 of suture 400 is then removed from slot 206 and is anchored outside the surgical site. No further steps are required using device 20 when tissue piece 404 is to be cut away and removed. Such removal is typically effected by severing tissue piece 404 by known methods and then pulling on the suture loop 400 threaded through the tissue piece whereby the latter is removed from the surgical site.

In the event the meniscus is to be manipulated to facilitate cutting or otherwise treating the meniscus, it may be advantageous to pass the end of suture 400 anchored outside the surgical site through a small ring attached to the end of a thin shaft and then manipulate the shaft so as to cause the ring to move along the suture until it is adjacent issue piece 404. By then moving the shaft laterally relative to its axis, the suture 400 captivated in the ring will move laterally as will the tissue piece which is anchored to the end of the suture by the slip knot. Thus, by selective manipulation of the shaft, the tissue piece may be moved to a position where the cutting or other treatment of the tissue is facilitated.

When it is desired to stitch tissue piece 404 to itself or to another tissue piece, one half of suture loop 400 is pulled through the opening in the tissue piece 404 so that a single length of suture extends throughout the opening. Then, the entire suture threading procedure described above and illustrated in FIGS. 10-15 is repeated at another location on tissue piece 400 or on another tissue piece using a portion of the single length of suture.

On completion of this second suture threading process, a loop of suture will extend through the opening formed at another location in tissue piece 400 or in the second tissue piece. One end of this loop is then pulled through this opening with the result that one end of the length of suture extends through the opening in tissue piece 400, an intermediate portion of the suture extends between this latter opening and the opening formed at the other location in piece 404 or in the second tissue piece, and the other end of the suture extends through the opening in the other location in piece 404 or in the second tissue piece. The two openings in tissue piece 404, or the opening in tissue piece 404 and the opening in the second tissue piece, as the case may be, are then stitched together by knotting the two ends of the suture adjacent the openings in the tissue.

To use the device 20 to wrap a piece of suture around a piece of tissue 405 such as a ligament, as illustrated in FIGS. 16-18, a loop of suture 400 is secured to the front bracket, positioned under shoulder 46, and clamped off on the device. Tool 20 is then inserted into the cannula and maneuvered so that tissue piece 405 is positioned to contact bottom wall 30 of bracket 26, and to extend perpendicularly to the axis of inner tube 102, as illustrated in FIGS. 16-18. The length of inner tube 102 is further selected so that when movable handle 304 is moved to extend substantially in parallel with fixed handle 302, front end 106 will nearly contact inner surface 44 of bracket leg 28, i.e., front end 106 will be spaced about 0.03 inches from surface 44. In this position, tissue piece 405 is secured between bottom wall 30 of bracket 26 and the bottom surface of the front portion of inner tube 102, as illustrated in FIG. 16.

After securing a loop of suture 400 around bracket 26 and clamping the tissue piece 405 in bracket 26, extractor assembly 200 is urged forwardly in inner tube 102 on top of tissue piece 405 and through bore 36 in bracket front wall 28, as illustrated in FIG. 17.

Then, after freeing suture 400 from clamp 322, extractor assembly 200 is withdrawn, capturing suture segment 402 in the process, as illustrated in FIG. 18. Then inner tube 102 is moved rearwardly to release the clamping force on tissue piece 405, and the device is manipulated to free the tissue piece from the tool. Device 20 is then removed from the surgical site, with segment 402 captivated in extractor 200 being simultaneously removed. At this point, the knotted end of suture 400 can be used to form a slip knot around the piece of tissue 405. The mid-length segment 402 is then detached from extractor slot 206 and is typically anchored outside of the surgical site. The slip knot can be tightened or the ligament manipulated using a shaft having a small ring attached to the end thereof, as described above.

ADVANTAGES OF THE INVENTION

The suture threading, stitching and wrapping device of the present invention possesses several advantages over known open and closed surgical tissue clamping, punching and suture threading, stitching and wrapping devices.

First, the present invention is a single instrument, designed for use in open or closed surgery, for threading a loop of suture through or around a tissue piece. Typically, several known surgical instruments must be employed to perform this threading function.

Second, the present invention is designed to permit a user to quickly and easily anchor a tissue piece to be removed during a surgical procedure with a loop of suture, before severing the tissue piece, so as to reduce significantly the possibility that the tissue piece will escape from the surgical site and lodge elsewhere in the joint undergoing surgery.

Third, the present invention permits suture threading, stitching, and wrapping of tissue located in an area of the surgical site where access is limited. For instance, where a piece of tissue to be threaded is spaced from a bone a distance insufficient to permit a conventional suture needle to be passed through the tissue, the device of the present invention can be advantageously employed to achieve such suture threading.

Fourth, the present invention provides an instrument for threading a loop of suture through or around a piece of tissue, wherein the tissue-receiving portion of the instrument (i.e., the clamping bracket 26) has a fixed configuration and does not need to change its configuration or expand in size in order to receive the tissue which is to be affixed to the suture.

Fifth, the present invention provides an instrument for threading a loop of suture through or around a piece of tissue, wherein the suture-manipulating shaft or needle 202 moves along a controlled and largely shielded pathway, so that the needle's location can always be carefully regulated by the surgeon and the surrounding tissue safeguarded.

Since certain changes may be made in the above apparatus without departing from the scope of the invention herein involved, it is intended that all matter contained in the above description or shown in the accompanying drawings shall be interpreted in an illustrative and not in a limiting sense.

What is claimed is:

1. A suturing device for passing a loop of suture material through a piece of tissue, said suturing device comprising:
   (a) clamping means for releasably clamping a piece of tissue, said clamping means comprising:
       an outer tube having a first end and a second end;
       a bracket including a leg, said bracket being attached to said outer tube so that said leg projects across the longitudinal axis of said outer tube adjacent said first end of said outer tube and spaced from said first end of said outer tube; and
       an inner tube having a first end and a second end, said inner tube being slidably disposed within said outer tube so that said first end of said inner tube can be advanced towards and away from said leg, whereby a piece of tissue can be clamped between said leg and said first end of said inner tube when said tissue is disposed between said leg and said first end of said inner tube and said first end of said inner tube is advanced towards said leg;
   (b) actuation means coupled to said clamping means for actuating said clamping means from a location spaced from said tissue;
   (c) suture support means for positioning and securing a segment of a loop of suture material having two free ends adjacent a first side of a piece of tissue clamped in said clamping means; and
   (d) extraction means for (1) piercing an opening in a piece of tissue clamped in said clamping means and (2) engaging said segment adjacent said first side of said piece of tissue and pulling said segment through said opening to a location remote from said piece of tissue so that said loop of suture material passes through said opening from said first side of said piece of tissue through to a second side of said piece of tissue.

2. A device according to claim 1 wherein said clamping means, said suture support means and said extraction means are sized so as to be insertable in a single conventional cannula of the type used in closed surgery.

3. A device according to claim 1 wherein said leg comprises an inside surface that is configured to engage said first side of a piece of tissue clamped in said clamping means, an outside surface, and an aperture extending through said leg from said inside surface to said outside surface, with said aperture being aligned with the longitudinal axis of said inner tube and being sized so as to pass said extraction means therethrough.

4. A device according to claim 3 wherein said suture support means comprises a groove provided in said outside surface of said leg and a clamp secured to said actuation means for securing said two free ends of said loop of suture material so as to secure said loop under tension to said device and thereby retain said segment in said groove.

5. A device according to claim 1 wherein said bracket comprises a bottom wall having first and second shoulders positioned on opposite sides of said bottom wall.

6. A device according to claim 3 wherein said extraction means comprises a shaft slidably disposed in said inner tube, said shaft having a hooked first end for (1) piercing an opening in a piece of tissue clamped in said clamping means and thereafter passing through said aperture in said leg, (2) engaging said segment adjacent said outside surface of said leg, and (3) maintaining engagement with said segment as said shaft is withdrawn from said aperture and said opening in said tissue.

7. A device according to claim 1 wherein said actuation means comprises:
 a fixed handle secured to said outer tube;
 a movable handle pivotally mounted to said fixed handle, said movable handle having linkage means coupled with said inner tube for transmitting motion from said movable handle to said inner tube so that when said movable handle is pivoted toward and away from said fixed handle, said first end of said inner tube is moved, respectively, toward and away from said leg.

8. A device according to claim 7 wherein said actuation means further comprises locking means for locking said movable handle in a selected, fixed relationship with said fixed handle.

9. A device according to claim 6 wherein said hooked first end of said shaft extends beyond said outside surface of said leg when engaging said segment secured by said suture support means, and further wherein said extraction means comprises travel limit means for limiting the travel of said shaft so that only a selected length of said shaft can extend through said aperture in said leg.

10. A device according to claim 9 wherein said selected length ranges from 0.125 inches to 0.375 inches.

11. A suturing device for passing a loop of suture material around a piece of tissue, said suturing device comprising:
 clamping means for releasably clamping a piece of tissue;
 actuation means coupled to said clamping means for actuating said clamping means from a location spaced from said tissue;
 suture support means for positioning and securing a segment of a loop of suture material adjacent a first side of a piece of tissue clamped in said clamping means; and
 extraction means for engaging said segment and pulling said segment over a piece of tissue clamped in said clamping means to a location remote from said piece of tissue so that said loop of suture material passes around said piece of tissue.

12. A method of passing a loop of suture material through a piece of tissue comprising the following steps:
 (1) providing a suturing device comprising:
  clamping means for releasably clamping a piece of tissue, said clamping means comprising an outer tube having a first end and a second end, a bracket attached to said outer tube and including a leg having an inside surface and an outside surface, wherein said leg includes a groove in its outside surface and has a bore extending through said leg adjacent said groove, said bracket being attached to said outer tube so that said bore is coaxial with said outer tube, and an inner tube slidably disposed within said outer tube, said inner tube having a first end;
  actuation means coupled to said inner tube for causing said inner tube to move axially between a forward position wherein said first end of said inner tube is advanced toward said leg, and a rearward position wherein said first end of said inner tube is withdrawn from said leg;
  clamp means for securing portions of a length of suture material to said actuation means; and
  a shaft slidably disposed in said inner tube and adapted to (1) pierce an opening in a piece of tissue disposed between said first end of said inner tube and said inside surface of said leg and pass through said bore in said leg and (2) engage a segment of a length of suture positioned in said groove and pull said segment through said bore and through the opening formed in a piece of tissue disposed between said first end of said inner tube and said inside surface of said leg to a location remote from said leg and said piece of tissue so that said length of suture material passes through said bore and said piece of tissue, said shaft including a front end having a hook;
 (2) positioning a segment of a length of suture material in said groove in said outside surface of said leg, pulling portions of said length of suture material adjacent said segment away from said groove and securing said portions of suture material to said clamp means so that those of said portions between said groove and said clamp means are under tension;
 (3) manipulating said suturing device so as to cause a piece of tissue having front and back surfaces to be received between said first end of said outer tube and said inside surface of said leg;
 (4) manipulating said actuation means so as to cause said inner tube to move toward said forward position until said first end of said inner tube engages said rear surface of said tissue and said front surface of said tissue engages said inside surface of said leg;
 (5) urging said shaft toward and through said piece of tissue and through said bore in said leg until said hook is adjacent said segment of suture material positioned in said groove, whereby said shaft forms an opening in said piece of tissue;
 (6) manipulating said shaft so as to captivate said segment of suture material in said hook of said shaft, freeing said portions of suture material from said clamp means, and withdrawing said shaft from said piece of tissue so as to cause said segment of suture material and said portions of said suture adjacent said segment of suture material to pass through said opening in said piece of tissue, past said back surface of said piece of tissue, and into said inner tube; and
 (7) operating said actuation means so as to cause said inner tube to move toward said rear position, thereby disengaging said inner tube from said piece of tissue, and manipulating said surgical device so as to disengage said piece of tissue from said bracket.

13. A method of wrapping a loop of suture material around an elongate piece of tissue comprising the following steps:
   a) providing a suturing device comprising:
      clamping means for releasably clamping a piece of tissue, said clamping means having (1) an outer tube, (2) a bracket attached to one end of said outer tube and including a leg having an inside surface and an outside surface, wherein said leg includes a groove in its outside surface and has a bore extending through said leg which is positioned adjacent said groove, and (3) an inner tube slidably disposed within said outer tube, said inner tube having a first end;
      actuation means coupled to said inner tube for causing said inner tube to move axially between a forward position and a rearward position;
      clamp means for securing portions of a length of suture material to said actuation means; and
      a shaft slidably disposed in said inner tube and adapted to (1) pass through said bore in said leg and (2) engage a segment of a length of suture positioned in said groove and pull said segment through said bore to a location remote from said leg, said shaft including a front end having a hook;
   b) positioning a segment of a length of suture material in said groove in said outside surface of said leg, pulling portions of said length of suture material adjacent said segment away from said groove and securing said portions of suture material to said clamp means so that those of said portions between said groove and said clamp means are under tension;
   c) manipulating said suturing device so as to cause an elongate piece of tissue having front and back surfaces to be received between said outer tube and said leg;
   d) manipulating said actuation means so as to cause said inner tube to move to said forward position and thereby extend above and captivate said piece of tissue between said bracket and said inner tube;
   e) urging said shaft toward and through said bore in said leg until said hook is adjacent said segment of suture material positioned in said groove;
   f) manipulating said shaft so as to captivate said segment in said hook of said shaft, freeing said portions of suture material from said clamp means, and withdrawing said shaft from said leg so as to cause said segment of suture material and portions of said suture material adjacent said segment of suture material to pass over said piece of tissue, past said back surface of said piece of tissue, and into said inner tube; and
   g) operating said actuation means so as to cause said inner tube to move to said rear position, whereby said inner tube does not extend above and captivate said piece of tissue, and manipulating said suturing device so as to disengage said piece of tissue from said suturing device.

14. In a suturing apparatus comprising suture means for positioning a suture relative to a piece of tissue and control means for operating said suture means, said control means being remotely located from said suture means,
   the improvements comprising:
      a) clamping means for releasably clamping a piece of tissue, said clamping means having (1) an outer tube, (2) a bracket attached to one end of said outer tube and including a leg having an inside surface and an outside surface, wherein said leg includes a groove in its outside surface and has a bore extending through said leg which is positioned adjacent said groove, and (3) an inner tube slidably disposed within said outer tube, said inner tube having a first end;
      (b) actuation means coupled to said inner tube for causing said inner tube to move axially between a forward position and a rearward position;
      (c) clamp means for securing portions of a length of suture material to said actuation means; and
      (d) a shaft slidably disposed in said inner tube and adapted to engage a segment of a length of suture positioned in said groove and pull said segment through said bore to a location remote from said piece of tissue so that said length of suture material is positioned relative to said piece of tissue.

15. A suturing device for passing a loop of suture material through a piece of tissue, said suturing device comprising:
   (a) clamping means for releasably clamping a piece of tissue;
   (b) actuation means coupled to said clamping means for actuating said clamping means from a location spaced from said tissue;
   (c) suture support means for positioning and securing a segment of a loop of suture material having two free ends adjacent a first side of a piece of tissue clamped in said clamping means; and
   (d) extraction means for (1) piercing a piece of tissue clamped in said clamping means and engaging said segment at said first side of said piece of tissue, and (2) pulling said segment through said piece of tissue to a location remote from said piece of tissue while said tissue is clamped in said clamping means, so that said loop of suture material passes through said tissue from said first side.

16. A suturing device for passing a loop of suture material through a piece of tissue, said suturing device comprising:
   (a) clamping means for releasably clamping a piece of tissue;
   (b) actuation means coupled to said clamping means for actuating said clamping means from a location spaced from said tissue;
   (c) suture support means for positioning and securing a segment of a loop of suture material having two free ends adjacent a first side of a piece of tissue clamped in said clamping means; and
   (d) extraction means for (1) piercing an opening in a piece of tissue clamped in said clamping means, (2) engaging said segment adjacent said first side of said piece of tissue, and (3) pulling said segment through said opening to a location remote from said piece of tissue so that said loop of suture material passes through said opening from said first side of said piece of tissue through to a second side of said piece of tissue, said extraction means being operable independently of said clamping means.

17. A suturing device for passing a loop of suture material through a piece of tissue, said suturing device comprising:
   (a) clamping means for releasably clamping a piece of tissue;

(b) actuation means coupled to said clamping means for actuating said clamping means from a location spaced from said tissue;

(c) suture support means for positioning and securing a segment of a loop of suture material having two free ends adjacent a first side of a piece of tissue clamped in said clamping means; and (d) extraction means for (1) piercing an opening in a piece of tissue clamped in said clamping means, (2) engaging said segment adjacent said first side of said piece of tissue, and (3) pulling said segment through said opening to a location remote from said piece of tissue so that said loop of suture material passes through said opening from said first side of said piece of tissue through to a second side of said piece of tissue, said extraction means and a portion of said clamping means being disposed in telescoping relation with one another.

18. A suturing device for passing a loop of suture material around a piece of tissue, said suturing device comprising:

(a) clamping means for releasably clamping a piece of tissue;

(b) actuation means coupled to said clamping means for actuating said clamping means from a location spaced from said tissue;

(c) suture support means for positioning and securing a segment of a loop of suture material having two free ends adjacent a first side of apiece of tissue clamped in said clamping means so that said suture material also extends below and adjacent to a bottom side of said piece of tissue and so that said two free ends extend adjacent to a second side of said piece of tissue; and (d) extraction means for (1) engaging said segment of a loop of suture material adjacent said first side of said piece of tissue clamped in said clamping means, and (2) pulling said segment over a top side of said piece of tissue clamped in said clamping means to a location remote from said piece of tissue so that said loop of suture material passes around said piece of tissue.

19. A suturing device for passing a loop of suture material around a piece of tissue, said suturing device comprising:

(a) clamping means for releasably clamping a piece of tissue;

(b) actuation means coupled to said clamping means for actuating said clamping means from a location spaced from said tissue;

(c) suture support means for positioning and securing a segment of a loop of suture material having two free ends adjacent a first side of a piece of tissue clamped in said clamping means so that said suture material also extends below and adjacent to a bottom side of said piece of tissue and so that said two free ends extend adjacent to a second side of said piece of tissue; and (d) extraction means for (1) engaging said segment of a loop of suture material adjacent said first side of said piece of tissue clamped in said clamping means, and (2) pulling said segment over a top side of said piece of tissue clamped in said clamping means to a location remote from said piece of tissue so that said loop of suture material passes around said piece of tissue, said extraction means being operable independently of said clamping means.

20. A suturing device for passing a loop of suture material around a piece of tissue, said suturing device comprising:

(a) clamping means for releasably clamping a piece of tissue;

(b) actuation means coupled to said clamping means for actuating said clamping means from a location spaced from said tissue;

(c) suture support means for positioning and securing a segment of a loop of suture material having two free ends adjacent a first side of a piece of tissue clamped in said clamping means so that said suture material also extends below and adjacent to a bottom side of said piece of tissue and so that said two free ends extend adjacent to a second side of said piece of tissue; and (d) extraction means for (1) engaging said segment of a loop of suture material adjacent said first side of said piece of tissue clamped in said clamping means, and (2) pulling said segment over a top side of said piece of tissue clamped in said clamping means to a location remote from said piece of tissue so that said loop of suture material passes around said piece of tissue, said extraction means and a portion of said clamping means being disposed in telescoping relation with one another.

* * * * *